United States Patent [19]

Hall

[11] Patent Number: 4,533,357
[45] Date of Patent: Aug. 6, 1985

[54] SANITARY NAPKIN CONSTRUCTION

[76] Inventor: Frances E. Hall, Highway 90E, Box 19, Del Rio, Tex. 78840

[21] Appl. No.: 487,184

[22] Filed: Apr. 21, 1983

[51] Int. Cl.³ .............................................. A61F 13/16
[52] U.S. Cl. ................................................... 609/401
[58] Field of Search ............... 604/386, 387, 399, 400, 604/385, 358, 359, 401, 402

[56] References Cited

U.S. PATENT DOCUMENTS 2,828,746  4/1958  Petuskey ............................ 604/399
3,126,888  3/1964  Woldman ............................ 604/399
3,769,979  11/1973  Freney ............................... 604/387
3,906,952  9/1975  Zamist ............................... 604/387
4,046,147  9/1977  Berg .................................. 604/387 X Primary Examiner—John D. Yasko
Attorney, Agent, or Firm—Browning, Bushman, Zamecki & Anderson

[57] ABSTRACT

A sanitary napkin having a pad portion and a tab portion projecting from said pad portion, the tab portion being received between the lower portion of the buttocks of the wearer to prevent escape of body fluid exudate past the posterior portion of the sanitary napkin.

5 Claims, 5 Drawing Figures

SANITARY NAPKIN CONSTRUCTION

BACKGROUND OF THE INVENTION

The present invention relates to a new and improved sanitary napkin for absorbing discharged body fluid exudate.

Numerous types of sanitary napkins and introvaginal tampon devices are known for use in controlling the discharge of body fluid exudate such as menstrual fluids. As is known, the common sanitary napkin is comprised of a pad of absorbent material which is generally elongate in configuration, the thickness of the pad varying with the type and absorbency of the material. It is common practice for the pad to be made of multiple layers of various materials to achieve desired results of absorbency and/or retention. While the sanitary napkins, which have been used for many years, are relatively effective in controlling menstrual fluid flow, they suffer from the disadvantage that during periods when the flow of menstrual fluid is heavy, such as during the start of the menstrual cycle, the fluid has a tendency to flow downwardly toward the buttocks if the woman is in a reclining position on her back. Thus, the fluid will flow past the posterior end of the pad and onto undergarments, bed sheets and the like. A like situation can occur when the woman remains seated for extended periods of time and the flow of menstrual fluid is heavy.

While catamenial devices such as introvaginal tampons, to a large extent, overcome the disadvantage discussed above with respect to ordinary sanitary napkins, they present a number of problems. For one, tampon devices are somewhat difficult to insert into the vaginal canal and therefore normally require special inserting means. Additionally, tampon devices have a tendency to swell as they absorb the menstrual fluid leading to (a) difficulty in removing the saturated tampon; and (b) leakage of the absorbed fluid due to squeezing of the device resulting in staining of garments and the like. Moreover, as recent events have shown, certain tampon devices may result in a condition known as toxic-shock syndrome which can be fatal.

U.S. Pat. No. 3,690,321 discloses a catamenial device comprised of a tampon portion and a pad portion, the tampon portion being received into the vaginal canal, the pad portion being seated between the labia majora of the vulva.

SUMMARY OF THE INVENTION

It is therefore an object of the present invention to provide an improved sanitary napkin which substantially prevents leakage of body fluid exudate past the posterior portion of the napkin.

Another object of the present invention is to provide an improved sanitary napkin which achieves the advantages of a tampon device without the necessity for the introvaginal insertion of an absorbing member.

The above and other objects of the present invention will become apparent from the drawings, the description given herein and the appended claims.

The sanitary napkin of the present invention is comprised of a generally elongate pad portion made of an absorbent material for absorbing body fluid exudate such as menstrual fluid. The pad portion has an anterior end and a posterior end and an absorbing surface side for generally overlaying and extending beyond the anterior and posterior ends of the labia majora of the wearer. Projecting from the absorbing surface side of the pad portion is a flexible tab portion, the tab portion being disposed rearwardly of the pad portion closer to the posterior end thereof. The tab portion has a length which is sufficient to be disposed between the lower portion of the buttocks of the wearer and is comprised of a soft, absorbent material to absorb the body fluid exudate. The tab portion is shaped or formed so as to comfortably be received between the buttocks and thus will preferably have a smooth configuration such as, for example, generally round in cross-section.

DESCRIPTION OF THE PREFERRED EMBODIMENTS

The sanitary napkin of the present invention, in general, comprises a pad portion which generally overlays the labia majora of the wearer and a tab portion projecting from the pad portion which can be disposed between the buttocks of the wearer to absorb body fluid exudate seeping past the posterior end of the pad portion.

Figure 1:
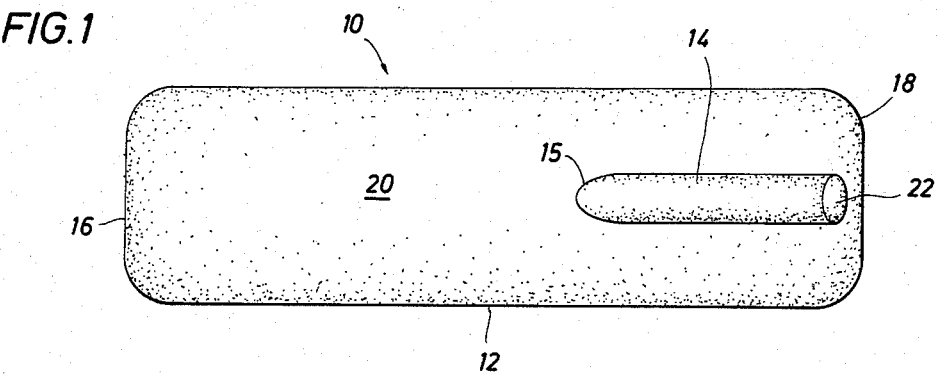
FIG. 1 is a planar view of the sanitary napkin of the present invention.
Figure 2:
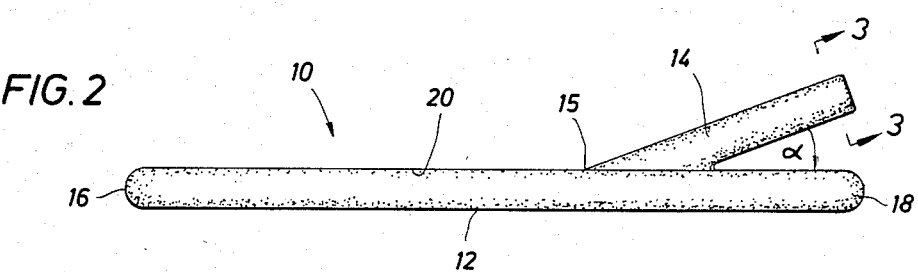
FIG. 2 is an elevational view of the sanitary napkin shown in FIG. 1.

Referring now to FIG. 1, the sanitary napkin, shown generally as 10, comprises a pad portion 12 and a tab portion 14 interconnected in a suitable fashion as at 15. Pad portion 12 is generally elongate in nature and, as shown, is generally rectangular although it will be recognized that the respective ends of pad portion 12 can be tapered to form a more oval, less rectangular configuration. Pad portion 12 has an anterior end 16 and a posterior end 18. Pad portion 10 is also provided with an absorbing surface side 20 from which tab portion 14 projects. As seen with reference to FIGS. 1 and 2, tab portion 14 is disposed closer to the posterior end 18 of pad portion 12 and, in the preferred embodiment, projects upwardly away from surface 20. While, as shown in FIG. 2, tab portion 14 is disposed at an angle to the surface 20 of pad 12 and projects generally toward the posterior end 18 of pad 12, it is to be understood that tab portion 14, being flexibly attached to pad portion 12, can lie at virtually any angle to the surface 20, the only requirement being that tab portion 14 and pad portion 12 be interconnected in a fashion which allows great flexibility of movement of tab portion 14 relative to pad portion 12.

Generally speaking, pad portion 12 and tab portion 14 will be made of some highly absorbent material such as, for example, cellulose wading or the like. However, it will be recognized that both tab portion 14 and pad portion 12 can be made from laminated layers of material having varying degrees of absorbency and fluid retention. Although tab portion 14 and pad portion 12 are generally formed into a unitary body in a suitable fashion such as by molding or other forming techniques, it will be recognized that tab portion 14 and pad portion 12 can be individually formed and then attached to one another in a suitable fashion so as to provide the required degree of flexibility of tab 14 relative to pad 12.

Tab portion 14, which is generally elongate, will preferably have a length which is sufficient to be received between the lower portion of the buttocks, but, as will be seen hereafter, will preferably be covered by the anterior end 18 of pad 12 when tab portion 14 is disposed between the buttocks of the wearer. Accordingly, and in the preferred case, the free end 22 of tab portion 14 will not extend past the posterior end 18 of pad portion 12 when tab portion 14 is compressed against surface 20. However, it will be recognized that tab portion 14 can be of a longer length, if desired, consistent with tab portion 14 being comfortably received between the buttocks of the wearer.

Figure 3:
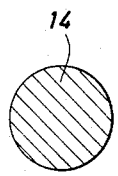
FIG. 3 is a cross-sectional view taken along the lines 3—3 of FIG. 2.
Figure 4:
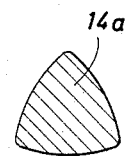
FIG. 4 is a view similar to FIG. 3 showing another cross-sectional configuration of the tab portion of the sanitary napkin of the present invention.

It is preferable that tab portion 14 have a cross-sectional configuration which will be comfortably received between the buttocks of the wearer and, to this end, tab portion 14 will generally have a smooth outer contour such as for example being round in cross-section such as shown in FIG. 3. Alternately, and in one of only many other configurations, tab portion 14 may have a cross-sectional configuration such as that of tab 14a shown in FIG. 4. It will be recognized that the configuration shown in FIG. 4 provides easy and comfortable insertion of tab portion 14a between the buttocks of the wearer. It will be apparent that numerous other cross-sectional configurations of tab portion 14 can be employed, the only requisite being that the shape be such as to be comfortable to the wearer. In this regard, tab portion 14 will be sized so as to be retained between the buttocks of the wearer, in normal use, and yet provide minimum or no discomfort.

Figure 5:
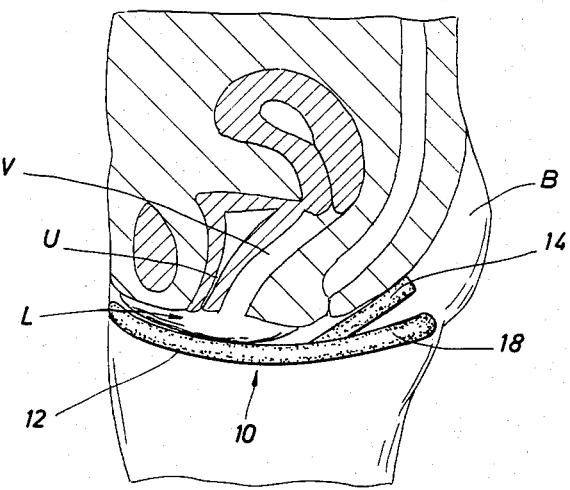
FIG. 5 is a diagrammatic view of the sanitary napkin of the present invention in its normal anatomical disposition.

Referring now to FIG. 5, the sanitary napkin of the present invention is shown in its normal anatomical disposition in the wearer. As can be seen, when sanitary pad 10 is properly in place, the pad portion 12 will generally overlay the labia majora L of the wearer and generally extend beyond the anterior and posterior ends thereof. Tab portion 14 will be received between the buttocks, the right buttock B of which is shown in FIG. 5. Menstrual fluid or other body fluid exudate from vaginal canal V or, in certain cases due to physiological disorders from urethral canal U, will be absorbed primarily by pad portion 12 of sanitary napkin 10. However, any such exudate or fluid which would have a tendency to flow into the crevice formed between the buttocks when the wearer is in a reclined or seated position will be absorbed by tab portion 14 thereby preventing such exudate from flowing past the posterior end 18 of pad portion 12 to soil undergarments, bed sheets or the like. While the sanitary napkin 10 of the present invention finds particular usage in preventing body fluid exudate such as menstrual fluid from flowing down between the buttocks when the wearer is in the reclining position, it will be recognized that the sanitary napkin 10 can be worn at all times, either day or night, since tab portion 14 presents no discomfort to the wearer because of its softness and contoured configuration.

To use the sanitary napkin 10, pad portion 12 is positioned in generally overlaying relationship to the labia majora and tab portion 14 gently pressed between the buttocks of the wearer either by simply pressing tab portion 14 into the crevice of the buttocks or by exerting pressure on the outer surface of pad portion 12 to gently urge tab portion 14 between the buttocks. In either event, when sanitary napkin 10 has been properly emplaced, tab portion 14, in the preferred case, will be covered by the anterior end 18 of pad portion 12.

It will be recognized that the construction of pad portion 12 and tab portion 14 can utilize any commonly used construction for sanitary napkins or catamenial devices. Pad portion 12 and tab portion 14 can also be constructed differently with varying absorption and fluid retention properties. Pad portion 12 can also include suitable adhesive surfaces either for securing pad portion 12 to the undergarment of the wearer or to portions of the body of the wearer.

The foregoing disclosure and description of the invention is illustrative and explanatory thereof, and various changes in the size, shape and materials as well as in the details of the illustrated construction may be made within the scope of the appended claims without departing from the spirit of the invention.

What is claimed is:

1. A sanitary napkin comprising a generally elongate pad portion comprising an absorbent material for body fluid exudate, said pad portion having an anterior end and a posterior end and an absorbing surface side for generally overlaying the labia majora of the wearer, and a flexible tab portion projecting from said absorbing surface side, said tab portion being disposed closer to said posterior end of said pad portion, said tab portion having a length and a shape sufficient to be comfortably disposed between at least the lower portion of the buttocks of the wearer, said tab portion being covered by the anterior portion of said pad portion when said tab portion is disposed between said buttocks, said tab portion being comprised of an absorbent material to absorb body fluid exudate.

2. The napkin device of claim 1 wherein the absorbent material of said pad portion and the absorbent material of said tab portion are the same.

3. The napkin device of claim 1 wherein said tab portion has a generally triangular shaped cross-sectional configuration.

4. The napkin device of claim 1 wherein said tab portion has a generally circular cross-sectional configuration.

5. The napkin device of claim 1 wherein said tab portion and said pad portion are integrally formed.

* * * * *